(12) United States Patent
Wang et al.

(10) Patent No.: US 8,071,125 B2
(45) Date of Patent: Dec. 6, 2011

(54) TRANSDERMAL PATCH CONTAINING ISOSORBIDE DINITRATE AND BISOPROLOL

(75) Inventors: Shuming Wang, Beijing (CN); Li Wang, Beijing (CN); Xiaoling Fan, Beijing (CN); Huiyong Xue, Beijing (CN); Shuang Zhang, Beijing (CN); Enhong Zhang, Beijing (CN); Xuying Zhong, Beijing (CN); Yucheng Lu, Beijing (CN); Chun Li, Beijing (CN); Li Song, Beijing (CN)

(73) Assignee: Beijing Kangbeide Pharmaceutical Technology Development Co., Ltd., Beijing (CN)

( * ) Notice: Subject to any disclaimer, the term of this patent is extended or adjusted under 35 U.S.C. 154(b) by 698 days.

(21) Appl. No.: 12/096,545

(22) PCT Filed: Dec. 9, 2005

(86) PCT No.: PCT/CN2005/002136
§ 371 (c)(1),
(2), (4) Date: Aug. 8, 2008

(87) PCT Pub. No.: WO2007/065303
PCT Pub. Date: Jun. 14, 2007

(65) Prior Publication Data
US 2008/0292685 A1    Nov. 27, 2008

(51) Int. Cl.
*A61F 13/00* (2006.01)
(52) U.S. Cl. ....................................................... 424/449
(58) Field of Classification Search ........................ None
See application file for complete search history.

(56) References Cited

U.S. PATENT DOCUMENTS 6,562,363 B1 * 5/2003 Mantelle et al. .............. 424/434
(Continued)

FOREIGN PATENT DOCUMENTS

CN    1102384 C    3/2003
(Continued)

OTHER PUBLICATIONS

Lui, W., "Analysis of Therapeutic Effect of the Compatibility of Metoprolol with ISOSORBIDE Dinitrate for the Treatment of Angina Pectoris" (1999) pp. 54, vol. 18(1), together with English Translation.

(Continued)

*Primary Examiner* — Robert A Wax
*Assistant Examiner* — Bethany Barham
(74) *Attorney, Agent, or Firm* — Scully, Scott, Murphy & Presser, P.C.

(57) ABSTRACT

This invention relates to a transdermal patch in the form of a layer complex, comprising a backing layer, a drug-reservoir layer comprising pharmacologically active ingredients and pharmaceutically acceptable adjuvants, and a release liner covering the drug-reservoir layer, characterized in that the drug-reservoir layer comprises isosorbide dinitrate and Bisoprolol at a ratio of 1:3 to 3:1 by weight, as the pharmacologically active ingredients. Animal tests show that said patch can reduce the elevation of T wave of cardiogram, the increase of the level of myocardial enzyme in blood serum, and the extension of the range of myocardial infarction caused by ligating the coronary artery in animals. Results show that said patch exhibits a considerable synergistic effect in the treatment of cardiovascular diseases and has good preventive and therapeutic effects on several adverse events on heart. In addition, the animal tests show that the patch according to the invention has a better pressure-reducing effect than the application of the patch containing only one of isosorbide dinitrate and Bisoprolol, and does not worsen the arrhythmia that is easily caused by the application of the patch containing only isosorbide dinitrate or Bisoprolol.

23 Claims, 1 Drawing Sheet

1 backing layer
2 drug-reservoir layer
3 drug release rate-controlling membrane layer
4 pressure-sensitive adhesive layer
5 covering layer

U.S. PATENT DOCUMENTS

2009/0203653 A1 * 8/2009 Garvey ..................... 514/149

FOREIGN PATENT DOCUMENTS

| EP | 1 329 225 A2 | 7/2003 |
|----|--------------|--------|
| EP | 1 462 121 A1 | 9/2004 |
| EP | 1 541 177 A1 | 6/2005 |
| GB | 1 213 211 | 11/1970 |

OTHER PUBLICATIONS

De Divitiis O. et al., "Bisoprolol in the Treatment of Angina Pectoris: A Double Blind Comparison with Verapamil", *European Heart Journal 8(supplement M)*:43-54 (1987).

Portegies M.C.M. et al., "Effects of Bisoprolol and Isosorbide Dinitrate on the Circadian Distribution of Myocardial Ischema", *Current Therapeutic Research* 56(12):1225-1236 (1995).

* cited by examiner

TRANSDERMAL PATCH CONTAINING ISOSORBIDE DINITRATE AND BISOPROLOL

TECHNICAL FIELD

This invention relates to the field of pharmaceutical formulations. Specifically, this invention relates to a transdermal patch containing isosorbide dinitrate and Bisoprolol as the active ingredients, and said transdermal patch can be used for the treatment of cardiovascular diseases.

BACKGROUND ART

Cardiovascular diseases mainly include heart paralysis, angina pectoris (myocardial infarction), arrhythmia, hemorrhagic heart failure, hypertension, stroke, congenital cardiac defect, rheumatic heart disease, and the like. Among those diseases, heart paralysis, stroke and hypertension are three most common diseases. Usually, possible factors causing risks of cardiovascular diseases are not present independently, but co-existent.

Isosorbide dinitrate, which is also known as Xiaoxintong, is mainly used for preventing and treating angina pectoris. In recent years, however, it also became a primary drug for treating heart failure. It acts on the specific receptor in the vascular smooth muscles and releases inorganic nitrate to relax the smooth muscles. A small dose of isosorbide dinitrate can expand the veins, and a large dose of isosorbide dinitrate can expand both the arteries and the veins. The expansion of the vein system can lower the preload and reduce the volume of the left ventricle so as to enhance the contractility of the cardiac muscles. Meanwhile, the reduction of the diastolic pressure in the heart chambers also lowers the resistance of the subendocardial coronary arteries, so that the blood-supply ability of the cardiac muscles is improved, the contractility of the cardiac muscles is enhanced, and the heart failure is alleviated. It can act instantly and has a reliable therapeutic effect, and is more convenient than other vasodilator drugs that need to be injected, such as phentolamine, nitroprusside sodium and the like. Therefore isosorbide dinitrate is a primary drug for treating heart failure.

However, a tolerance to isosorbide dinitrate may be caused if this drug is administered continuously. Consequently, the therapeutic effect may be diminished or disappear. It is mentioned in Drugs for Heart primarily translated by Gao Wei et al. ($4^{th}$ edition, Liaoning Education Press, September of 1999, page 48) that if long acting nitric acid ester drugs are regularly administered for a long period of time without intermission or dosing peak period, it is very easy for this kind of drugs to cause tolerance, and the effect of said drugs cannot be persistent. If isosorbide dinitrate is administered four times a day in a dosage of 30 mg each time for a long period of time, the effect thereof on treating angina pectoris will be quickly weakened because of the tolerance. This literature and all publications or literatures as mentioned below are incorporated into the specification by reference.

Bisoprolol is a $\beta_1$ receptor blocking agent having high affinity and selectivity to receptor of heart. Compared with $\beta$ receptor blocking agents that do not have selectivity, Bisoprolol can prevent adverse effects on pulmonary functions, blood lipid and peripheral circulation caused by $\beta_2$ receptor blocking.

However, the oral administration of Bisoprolol will cause some adverse effects. Liu Guoshu et al. (Clinical Observations of 228 Patients with Primary Hypertension Treated with Bisoprolol, Journal of Cardiopulmonary Vascular Diseases, $3^{rd}$ issue, vol. 18, 1999, pages 179 to 182) reported that the oral administration of Bisoprolol had good pressure-reducing effects but would greatly affect the heart rate. The average reduction of the heart rate after the treatment was 15.1%. Moreover, the higher the dosage was, the lower the heart rate would be. Common adverse effects, such as sinoatrial bradycardia, complete right bundle branch block, atrial premature, nausea and acratia, and short P-R interval syndrome, were exhibited in some patients. It shows that Bisoprolol should be administrated orally with discretion to the patients with a slow heart rate.

People also tried to treat angina pectoris by the combination of Bisoprolol with long acting nitric acid ester drugs.

Mireille C. M. Portegies et al. (Mireille C. M. Portegies, Jan Brouwer, Louis L. M. V. D. Ven, Jan W. Viersma, and Kong I. Lie, "Effect of Bisoprolol and Isosorbide Dinitrate on the Circadian Distribution of Myocardial Ischemia", Current Therapeutic Research, 1995, (56), 1225-1236) compared the results of treating athletic type angina pectoris and myocardial ischemia with isosorbide dinitrate and Bisoprolol independently and the combination thereof. Bisoprolol was administered orally once a day in a dosage of 10 mg, and isosorbide dinitrate was administered orally thrice a day in a dosage of 20 mg. The drugs were administered continuously for 4 weeks. Results showed that the effect of the combination of the drugs was just the addition of the effects of said two independent drugs and did not exhibit a significant synergistic effect on the symptoms studied.

O. DE Divitiis et al. (O. DE Divitiis, V. Liguori, S. Di Somma, et al., "Bisoprolol in the Treatment of Angina Pectoris: a Double Blind Comparison with Verapamil", European Heart Journal, 1987, 8 (Suppl. M), 43-54)) compared the pharmaceutical effect of the combination of Bisoprolol and isosorbide dinitrate (1:4 to 1:2) on the treatment of angina pectoris with that of the combination of Isoptin and isosorbide dinitrate (6:1 to 9:1) and discovered that like Isoptin, Bisoprolol was also effective on treating myocardial ischemia and the patients had a good tolerance to it.

A transdermal patch is a pharmaceutical formulation that can be percutaneously applied. Liang Bingwen indicates in Transdermal Drug Delivery Formulation (China Medical-Pharmaceutical Science & Technology Publishing House, published in September 1992, pages 13-14) that compared with conventional administering methods, the transdermal drug delivery system has the following characteristics. (1) The drug can enter the body at a constant rate during a long period of time, which is similar to a long term intravenous drip. (2) The first pass effect of the liver and the interference and degradation effects of the gastrointestinal tract factors can be avoided. These factors are also main reasons for individual effective differences caused by the oral administration of drugs. The transdermal drug delivery system can reduce individual differences (3) The permeating rate of drugs is the same as the rate of elimination in vivo. A constant and effective plasma drug concentration can be maintained. Consequently, the fluctuation of plasma drug concentration caused by other administering methods can be avoided, and adverse effects of the drugs can be decreased. (4) It's very convenient for patients to use the transdermal drug delivery system. It is more suitable for patients to whom the oral administration is not appropriate and patients who need to administer a drug for a long period of time.

There are literatures reporting transdermal patches containing either isosorbide dinitrate or Bisoprolol alone (Hidaka Osafumi, Isosorbide Dinitrate-Containing Patch, Chinese Patent No.: ZL98800181.0, Tateishi Tetsuro, et al., Adhesive Patch, WO2005011662; SAEKI YUJI, et al., Bisoprolol-Containing Plaster, JP2003313122).

However, the prior arts have not disclosed any transdermal pharmaceutical formulations containing both isosorbide dinitrate and Bisoprolol by far.

The inventors of this invention have discovered that in transdermal patches containing isosorbide dinitrate and Bisoprolol at special ratios, said drugs exhibit an unexpected synergistic effect. Compared with transdermal patches containing either isosorbide dinitrate or Bisoprolol alone, the combination of isosorbide dinitrate and Bisoprolol at said special ratios exhibits excellent effects on preventing and treating a variety of heart diseases and a better pressure-reducing effect and improves the arrhythmia caused by transdermal patches containing either isosorbide dinitrate or Bisoprolol. Therefore the inventive patches show advantages in the treatment of cardiovascular diseases.

Contents of the Invention

The object of this invention is to provide a transdermal patch comprising isosorbide dinitrate and Bisoprolol at a special ratio for treating cardiovascular diseases. Isosorbide dinitrate and Bisoprolol at said ratio exhibit a synergistic effect.

Consequently, this invention relates to a transdermal patch in the form of a complex layer comprising a backing layer, a drug-reservoir layer comprising pharmacologically active ingredients and pharmaceutically acceptable adjuvants, and a release liner covering the drug-reservoir layer, characterized in that the drug-reservoir layer comprises isosorbide dinitrate and Bisoprolol at a ratio of 1:3 to 3:1 by weight, preferably 1.2 to 1.8:1, most preferably 1.4 to 1.6:1 by weight.

In the transdermal patch according to this invention, the backing layer consists of back supporting materials well known to a person skilled in the art, such as an aluminum foil, polyethylene terephthalate, polyethylene or non-woven fabrics.

In the transdermal patch according to this invention, the pharmaceutically acceptable adjuvants include a permeation enhancer and a polymeric matrix, wherein the polymeric matrix is, for example, selected from the group consisting of an acrylic pressure-sensitive adhesive and a combination of an acrylic pressure-sensitive adhesive with an Eudragit-type acrylic resin.

In this application, the term "an acrylic pressure-sensitive adhesive" refers to a polymer well known in the art formed by copolymerizing acrylic acid and derivatives thereof. Said polymer has a saturated carbon-hydrogen primary chain and an ester side chain. A sticky acrylic pressure-sensitive adhesive can be produced by modifying comonomers and side chain groups. Common monomers include acrylic acid, butyl acrylate, 2-ethylhexyl acrylate, vinyl acetate, 2-hydroxyethyl acrylic acid and the like. The polymerization reaction can be performed in a solution (Liang Bingwen, Transdermal Drug Delivery Formulation, China Medical-Pharmaceutical Science & Technology Publishing House, published in September 1992, pages 230-232; Yang Yukung, Pressure-Sensitive Adhesives, Chapter 5, An Acrylic Ester Pressure-Sensitive Adhesive, Science Press, published in May of 1991, pages 148-210; and Wang Shuming, CN1640500A).

With regard to said "Eudragit-type acrylic resin", non-limiting examples include Eudragit® L100, Eudragit® S100, Eudragit® RL100, Eudragit® RS100, Eudragit® E100, Eudragit® L100-55, Eudragit® E PO, Eudragit® RL PO, Eudragit® RS PO and the like manufactured by Röhm Co. Ltd. (Germany).

In the preferred embodiments of the transdermal patch according to this invention, the polymeric matrix is a mixture of an acrylic pressure-sensitive adhesive with an Eudragit-type acrylic resin.

In this application, the term "permeation enhancer" is a substance well known in the art that can overcome the barrier effect of the skin and increase the transdermal flux of a drug or the transdermal amount of a drug, including surfactants, organic solvents, such as alcohols, e.g. propylene glycol (PG), esters, dimethyl sulfoxide and analogs thereof, azone compounds, organic acids and esters or amides thereof, etc. (Liang Bingwen, Transdermal Drug Delivery Formulation, Chapter 5, Transdermal Permeation Enhancers and its application thereof, China Medical-Pharmaceutical Science & Technology Publishing House, published in September 1992, pages 116-164). Non-limiting examples of said permeation enhancers include isopropyl myristate, Azone, propylene glycol and the like and a mixture thereof.

In one embodiment of the transdermal patch according to this invention, the drug-reservoir layer consists of, based on the total weight of the drug-reservoir layer, the following substances:

| | |
|---|---|
| isosorbide dinitrate | 1-17% |
| Bisoprolol | 1-17% |
| Eudragit RS100 | 0.1-30% |
| acrylic resin pressure-sensitive adhesive (in dry basis) | 30-80% |
| propylene glycol | 0-25% |
| isopropyl myristate | 4.5-22% |
| Azone | 1.5-7% |
| and the sum thereof is 100%. | |

In one preferred embodiment of the transdermal patch according to this invention, the drug-reservoir layer consists of, based on the total weight of the drug-reservoir layer, the following substances:

| | |
|---|---|
| isosorbide dinitrate | 2.5-15% |
| Bisoprolol | 2-8% |
| Eudragit RS100 | 0.5-25% |
| acrylic resin pressure-sensitive adhesive (in dry basis) | 45-65% |
| isopropyl myristate | 6-10% |
| Azone | 4-6% |
| and the sum thereof is 100%. | |

In one particularly preferred embodiment of the transdermal patch according to this invention, the drug-reservoir layer consists of, based on the total weight of the drug-reservoir layer, the following substances:

| | |
|---|---|
| isosorbide dinitrate | 3.6-10% |
| Bisoprolol | 2.6-6% |
| Eudragit RS100 | 3-25% |
| acrylic resin pressure-sensitive adhesive (in dry basis) | 45-65% |
| isopropyl myristate | 6-10% |
| Azone | 4-6% |
| and the sum thereof is 100%. | |

In another embodiment of the transdermal patch according to this invention, the drug-reservoir layer consists of the following substances by weight.

| | |
|---|---|
| isosorbide dinitrate | 0.5-2 parts by weight |
| Bisoprolol | 0.4-1.1 parts by weight |
| Eudragit RS100 | 0.1-3.5 parts by weight |
| acrylic resin pressure-sensitive adhesive (in dry basis) | 5-10 parts by weight |

-continued

| | |
|---|---|
| isopropyl myristate | 0.5-2 parts by weight |
| Azone | 0.2-0.6 part by weight. |

In another embodiment of the transdermal patch according to this invention, the drug-reservoir layer consists of the following substances:

| | |
|---|---|
| isosorbide dinitrate | 0.5-1.3 parts by weight |
| Bisoprolol | 0.35-0.8 part by weight |
| Eudragit RS100 | 0.5-3.5 parts by weight |
| acrylic resin pressure-sensitive adhesive (in dry basis) | 6-8 parts by weight |
| isopropyl myristate | 1-1.5 parts by weight |
| Azone | 0.2-0.6 part by weight. |

In another embodiment of the transdermal patch according to this invention, the drug-reservoir layer consists of the following substances:

| | |
|---|---|
| isosorbide dinitrate | 0.5-0.7 part by weight |
| Bisoprolol | 0.4 part by weight |
| Eudragit RS100 | 0.25-3.5 parts by weight |
| acrylic resin pressure-sensitive adhesive (in dry basis) | 6-8 parts by weight |
| isopropyl myristate | 1-1.5 parts by weight |
| Azone | 0.2-0.6 part by weight. |

In another embodiment of the transdermal patch according to this invention, the drug-reservoir layer consists of the following substances:

| | |
|---|---|
| isosorbide dinitrate | 0.6 part by weight |
| Bisoprolol | 0.4 part by weight |
| Eudragit RS100 | 3 parts by weight |
| acrylic resin pressure-sensitive adhesive (in dry basis) | 6-8 parts by weight |
| isopropyl myristate | 1-1.5 parts by weight |
| Azone | 0.4 part by weight. |

In another preferred embodiment of the transdermal patch according to this invention, the drug-reservoir layer consists of the following substances:

| | |
|---|---|
| isosorbide dinitrate | 1.0-1.5 parts by weight |
| Bisoprolol | 0.8 part by weight |
| Eudragit RS100 | 0.25-3.5 parts by weight |
| acrylic resin pressure-sensitive adhesive (in dry basis) | 6-8 parts by weight |
| isopropyl myristate | 1-1.5 parts by weight |
| Azone | 0.2-0.6 part by weight. |

In another embodiment of the transdermal patch according to this invention, the drug-reservoir layer consists of the following substances:

| | |
|---|---|
| isosorbide dinitrate | 1.2 parts by weight |
| Bisoprolol | 0.8 part by weight |
| Eudragit RS100 | 3 parts by weight |
| acrylic resin pressure-sensitive adhesive (in dry basis) | 6-8 parts by weight |
| isopropyl myristate | 1-1.5 parts by weight |
| Azone | 0.4 part by weight. |

The transdermal patch according to this invention can be produced by any techniques known in the art, such as manufacture processes indicated by Liang Bingwen in Transdermal Drug Delivery Formulations (China Medical-Pharmaceutical Science & Technology Publishing House, published in September 1992, pages 328-337), such as, dissolving isosorbide dinitrate and Bisoprolol in an organic solvent, mixing the solution obtained with a solution comprising an permeation enhancer, mixing the obtained mixture with a solution comprising a polymeric matrix, coating the resultant to a back supporting material by a coating equipment comprising a roller coating type, a doctor knife coating type or by hand-coating, and then drying it. After that, the various layers of the product are laminated, died cut and packed.

Figure 1:
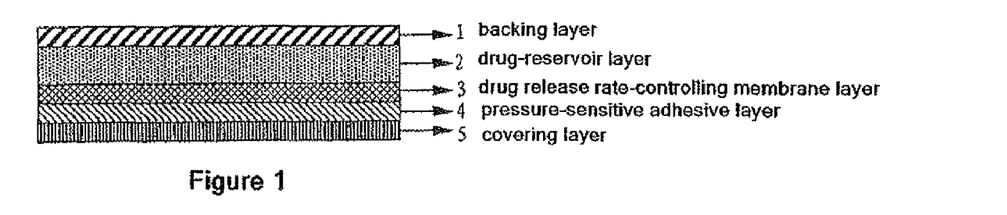
FIG. 1 illustrates the transdermal patch according to this invention in the membrane-reservoir type.
Figure 2:
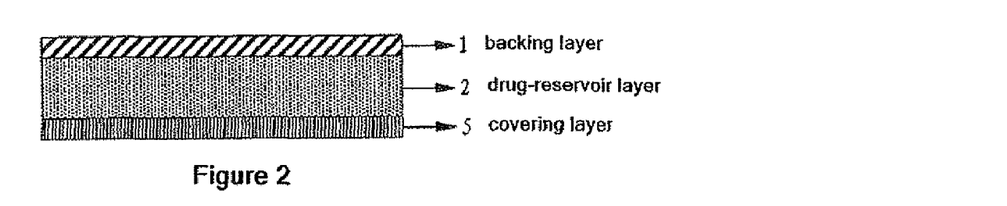
FIG. 2 illustrates the transdermal patch according to this invention in the skeleton-controlled release type.
Figure 3:
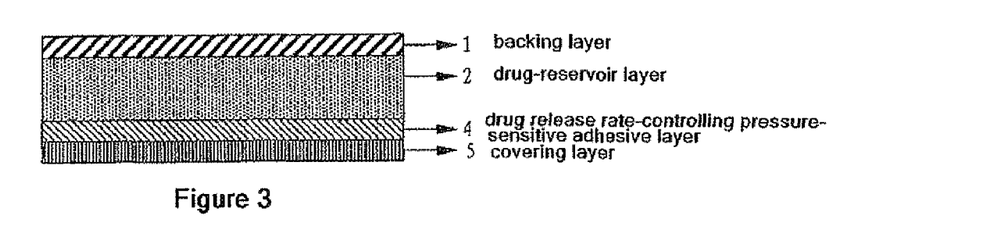
FIG. 3 illustrates the transdermal patch according to this invention in the adhesive-controlled release type.

The structure of the transdermal patch according to this invention can be a membrane-reservoir type, skeleton-controlled release type, and adhesive-controlled release type, wherein the drug-reservoir layer can be in the form of a mono-layer or multi-layered complex. Specific structures comprise, for example, a backing layer, a drug-reservoir layer, a drug release rate-controlling membrane layer, a pressure-sensitive adhesive layer (comprising a minor amount of the drugs or free of a drug), and a covering layer (FIG. 1); a backing layer, a drug-reservoir layer and a covering layer (FIG. 2); and a backing layer, a drug-reservoir layer, a drug release rate-controlling pressure-sensitive adhesive layer (comprising a minor amount of the drugs or free of a drug), and a covering layer (FIG. 3).

Tests of the transdermal patch according to this invention on animals show that the transdermal patch according to this invention can reduce the elevation of T wave of cardiogram, the increase of the level of myocardial enzyme in blood serum, the extension of the range of myocardiac infarction caused by ligating the coronary artery in animals. The results show that the transdermal patch according to this invention exhibits good therapeutic and preventive effects on several heart-diseases. In addition, animal tests also show that it not only has a better effect on reducing the blood pressure than the application of the patch containing either isosorbide dinitrate or Bisoprolol, but also improves or does not worsen the arrhythmia caused by the application of the patch containing only one of isosorbide dinitrate and Bisoprolol. Thus, it is shown that the combination of isosorbide dinitrate and Bisoprolol in the transdermal patch according to this invention, exhibits a considerable synergistic effect in the treatment of cardiovascular diseases. The combination of isosorbide dinitrate and Bisoprolol at said ratios has certain advantages in treating cardiovascular diseases.

The transdermal patch according to this invention is suitable for local application in the treatment or prevention of hypertension, coronary heart disease, atherosclerosis, myocardial ischemia or angina pectoris etc. in mammals. Generally, the dosage per day is based on the total weight of isosorbide dinitrate and Bisoprolol, 0.05-20 mg/kg body weight, preferably 0.5-10 mg/kg body weight, and particularly preferred 1-5 mg/kg body weight.

EXAMPLES

This invention is illustrated, but not limited by the following Examples. Obviously, a person skilled in the art can make any improvements, modifications and substitutions of the technical features concerned in the embodiments according to this invention under the spirit of this invention. All these improvements, modifications, and substitutions should be included within the spirit and scope according to this invention.

Examples 1 to 7 and Comparative Examples 1 and 2

Examples 1 to 7: a transdermal patch comprising the combination of isosorbide dinitrate and Bisoprolol.

Comparative example 1: a transdermal patch merely comprising individual isosorbide dinitrate.

Comparative example 2: a transdermal patch merely comprising individual Bisoprolol.

Said transdermal patches comprise, in total, 1 mg/cm$^2$ (a low dosage patch) or 2 mg/cm$^2$ (a high dosage patch) of isosorbide dinitrate and/or Bisoprolol, which are fed in an amount necessary for the production of 1000 cm$^2$ of patches.

(1) Formula

The specific combinations of Bisoprolol and isosorbide dinitrate are listed in Table 1.

TABLE 1

The Examples of the combinations of Bisoprolol and isosorbide dinitrate

| Example | Isosorbide dinitrate/ Bisoprolol | Isosorbide dinitrate/Bisoprolol (g/g) |
|---|---|---|
| Example 1 | 1:3 | 0.25/0.75 (or 0.5/1.5) |
| Example 2 | 1:2 | 0.33/0.67 (or 0.66/1.34) |
| Example 3 | 2:3 | 0.4/0.6 (or 0.8/1.2) |
| Example 4 | 3:2 | 0.6/0.4 (or 1.2/0.8) |
| Example 5 | 1:1 | 0.5/0.5 (or 1.0/1.0) |
| Example 6 | 2:1 | 0.67/0.33 (or 1.34/0.66) |
| Example 7 | 3:1 | 0.75/0.25 (or 1.5/0.5) |
| Comparative example 1 | 1:0 | 1/0 g (or 2/0) |
| Comparative example 2 | 0:1 | 0/1 g (or 0/2) |
| Blank control | 0:0 | 0/0 g |

Other pharmaceutically acceptable adjuvants in the drug-reservoir layer are fed in an amount necessary for the production of 1000 cm$^2$ of patches. The formula is as follows:

Eudragit RS100: 3 g
Acrylic pressure-sensitive adhesive (dry adhesive substrate): 8 g
Azone: 0.4 g
isopropyl myristate: 1.5 g
ethyle acetate: q.s.
Patches produced: 1000 cm$^2$.

(2) Production of the Patches (i) Formulation of the Drug-Reservoir Mixture

An appropriate amount of ethyl acetate was added to isosorbide dinitrate (Shandong Boshan Pharmaceutical Company, Batch No.: 010124) and Bisoprolol (which is produced by the following steps: netrualizing and alkalifying an aqueous solution of Bisoprolol Formarate (Beijing Biphenyl Chemical Technology Ltd., Batch No.: 050401) with sodium carbonate (Beijing Shijihongxing Chemicals Ltd., analytically pure, Batch No.: 011213) to remove fumarate, extracting said solution with ethyl acetate (Beijing Chemical Plant, analytically pure, Batch No.: 20020531), and distilling the organic phase under a reduced pressure (170-175° C./0.005–0.01 kPa)) in an amount required in the formula with stirring until the drugs were dissolved to produce a clear solution. Azone (Beijing Second Pharmaceutical Plant, Brand of Yanjing, Batch No.: 041201) and isopropyl myristate (Fine Chemicals Ltd., Hanyan County, Zhejiang Province, Batch No.: 25484958-1) in an amount required in the formula were added to said solution. This solution was stirred for 5 minutes to produce a clear liquid A.

An appropriate amount of ethyl acetate was added to the acrylic resin Eudagit® RS100 (Röhm GmbH Co. Ltd., Germany, Batch No.: 8310808118). The solution was stirred until the resin was dissolved, followed by the addition of acrylic pressure-sensitive adhesive in an amount required in the formula (which was produced from the monomers 2-ethyl hexyl acrylate (Shanghai Fuzhe Chemical Ltd., industrial grade), butyl acrylate (Beijing Xingjin Chemical Plant, analytically pure, Batch No.: 20011110) and vinyl acetate (Beijing Chemical Reagent Company, chemically pure, Batch No.: 050422) using ethyl acetate as a solvent according to the method as described in Pressure-Sensitive Adhesive (published by Science Press, May of 1991, complied by Yang Yukun, page 187), the solid content is 40%). This mixture was stirred for 5 minutes to produce a clear liquid B.

Liquid A was added to liquid B by stirring, followed by the addition of an appropriate amount of ethyl acetate to adjust the volume of the mixture to 60 ml. This solution was evenly stirred to produce a clear liquid C. Said liquid C was made to stand still so as to remove bubbles.

(ii) Coating

After the bubbles in said liquid C disappeared, said liquid C was manually coated to the back supporting material polyethylene terephthalate (Jiangyin Propack Company) to form a coated sheet. The coating rate was approximately 10 m/min, and the thickness of the coating was 0.60 mm.

(iii) Drying

The coated sheets were placed into an oven in which the temperature was programmed from 40° C. (0.5 hour) to 60° C. (1.5 hours) to remove the solvent. Transparent viscous patches were obtained after being cool.

(iv) Lamination

The dried sheets were laminated with anti-adhesion paper to form patches.

(v) Die Cut and Packaging

The laminated transdermal patches were died cut to form square patches having a desired area which were then sealed and stored in a paper-aluminum sack.

Examples of studies on pharmacodynamics on animals

Animal tests were conducted with blank control patches and the transdermal patches as described in Examples 1 to 7 and Comparative examples 1 and 2.

Two animal models were used, i.e. renal hypertensive rats (RHR, two-kidney, one clip) and spontaneous hypertensive rats (SHR). Said two animal models were treated by conscious acute pressure-reducing method, and the spontaneous hypertensive rats were treated with therapeutically pressure-reducing method. Effects of the transdermal patches as described in Examples 1 to 7 and Comparative examples 1 and 2 on the acute pressure-reduction of RHRs and SHRs and on the therapeutically pressure-reduction of SHRs were observed.

The coronary artery of SD rats was ligated. Influences of the transdermal patches of this invention on the raising of T wave in the electrocardiogram, the increase of the myocardial enzyme level in blood serum and the extension of the area of the cardiac infarction were observed.

Test 1. Studies of effects of the acute pressure-reduction on the renal hypertension rats 1. Object of the Test The object of this test is to observe the acute pressure-reducing effects of the transdermal patches as described in Examples 1 to 7 and Comparative examples 1 and 2 on renal hypertensive rats (RHRs).

2. Animals and Groups 2.1. Animals to be Tested

SD rats were provided by the Department of Experimental Animal Science of Fudan University with the certificate Number of SCXK (Hu) 2002-002. The animals' body weight was from 180 to 220 g. All rats were male.

2.2. Grouping of Animals

The RHRs were evenly and randomly divided into 10 groups according to their blood pressures, each group containing 7 to 10 rats. Said groups were respectively a blank patch control group, groups of the transdermal patch of Examples 1 to 7, and groups of the transdermal patch of Comparative examples 1 and 2.

3. Main Experimental Steps 3.1. Experimental Apparatus

The apparatus was BESN-II multiple-channel and non-invasive to an animal manometric system made by Nanjing DeSci Biotech Ltd. Co.

3.2. Preparation of a Renal Hypertensive Rat Model (RHR, Two-Kidney, One Clip)

Healthy male SD rats weighing from 180 to 220 g were anaesthetized with ethyl ether and then were fixed on a foamed plastic plate on their backs with their abdomens exposed to the outside. The surgical apparatus, gauze and cotton were boiled or sterilized in an oven at a temperature of 105° C. Hairs in an area of 2.5 to 3.5 cm long and 1.5 to 2 cm wide at the left side of the abdomen where the kidney was located were cut longitudinally. The skin was sterilized by iodine and 75% ethanol and then was cut longitudinally 2 to 2.5 cm long. Muscles were bluntly separated with hemostatic forceps to expose the kidney. The kidney was pulled out of the body with forceps. The renal artery was carefully separated by a glass dissecting needle. The renal artery was surrounded by a U-shaped steel clip having an inner diameter of 0.20 mm and a thickness of 0.5 mm and then the kidney was put back into the body. Thus, the surgery for narrowing the renal artery was finished. The muscles and the skin were carefully stitched respectively. The wound was sterilized with iodine swabs and bandaged with sterilized gauze. After the surgery, sodium penicillin (0.48 g, 800 thousand units, Shandong Lukang Pharmaceutical Co. Ltd., Guoyaozhunzi No. H37020079, batch number of production: B030605) at 20 thousand units/rat was administrated intra-abdominally to prevent infection.

After the surgery, the animals were fed with 1% saline for two consecutive weeks and then 0.5% saline for another week. The blood pressure of the rats could be measured 3 to 5 days after that period. First, the blood pressure was consecutively measured for three times. Animals were recognized to have renal hypertension as long as the systolic arterial pressure (SAP) was higher than 160 mmHg (21.3 kPa), otherwise, the animals were discarded. The rate of successfully producing this kind of animal model was more than 80%. The blood pressure was stable after the renal hypertension was formed. Generally, SAP could reach about 160 to 200 mmHg (21.3 to 26.7 kPa).

3.3. The Method for Measuring the Blood Pressure of Conscious Rats

A "BESN-II multiple-channel and non-invasive to an animal manometric system" was used in the non-invasive measurement of the blood pressure. After the measurement, the data of the systolic arterial pressure (SAP), diastolic pressure (DAP) and heart rate (HR) were collected.

In the acute pressure-reducing tests, the blood pressure was measured for more than 7 days (at least three times), so that the animals would be accustomed to the environment for measuring the blood pressure. After that, tests on the acute pressure-reducing effects were performed. The blood pressure was measured once before the application of the patches, and the blood pressure and heart rate were recorded. The blood pressure was measured 4 to 6, 9 to 11, 14 to 16, 19 to 21, 27 to 29, 34 to 36, 44 to 46, 50 to 52 and 59 to 61 hours after the application of the patches. Changes of the blood pressure and heart rate before and after the application of the patches were recorded.

4. Dosages

The transdermal patches in Examples 1 to 7 and Comparative examples 1 and 2 were applied in a dosage of 10.0 mg of isosorbide dinitrate and Bisoprolol in total/kg of body weight. Blank patches with an area of 10.0 cm²/kg body weight were used in the blank control group.

5. The Method for the Application of the Patches

Hairs on the back of the rats in an area of 5×5 cm² were removed with 10% sodium sulfide one day prior to the application of the patches. The patches to be tested were applied to the naked skin of the rats and then fastened with a medical adhesive tape.

6. Test Results

Effects of the transdermal patches in Examples 1 to 7 and Comparative examples 1 and 2 on reducing the blood pressure of the renal hypertensive rats were observed. Since the pharmaceutical effect was the most stable and potent 15 to 28 hours after the application of the patches, test results of 15 to 28 hours after the application of the patches were used. The test results were represented by mean±standard deviation (X±SD). With regard to the statistical treatment, student-T tests among groups were used. The results are shown in tables 2 to 4.

TABLE 2

Changes of the systolic arterial pressure of the renal hypertensive rats after the application of the patches

| Examples | Number of samples (kPa) | changes of the systolic arterial pressure 15 to 28 hours after the application of the patches (kPa) |
|---|---|---|
| Example 1 | 8 | −3.08 ± 1.97**$$## |
| Example 2 | 7 | −2.18 ± 1.81**$$## |
| Example 3 | 8 | −1.93 ± 1.21**$$## |
| Example 4 | 8 | −2.46 ± 1.23**$$## |
| Example 5 | 8 | −1.87 ± 1.12**$$## |
| Example 6 | 8 | −0.95 ± 1.32** |
| Example 7 | 8 | −1.17 ± 1.35** |
| Comparative example 1 | 8 | −0.45 ± 1.17** |
| Comparative example 2 | 7 | −0.98 ± 1.37** |
| Blank control group | 9 | 0.74 ± 1.20 |

Note:
*$P < 0.05$;
**$P < 0.01$; compared with the blank control group
$$P < 0.05$;
$$$P < 0.01$; compared with Comparative example 2
$P < 0.05$;
$P < 0.01$; compared with Example 1

TABLE 3

Changes of the diastolic pressure of the renal hypertensive rats after the application of the patches

| Examples | Number of samples | changes of the diastolic pressure 15 to 28 hours after the application of the patches (kPa) |
|---|---|---|
| Example 1 | 8 | −2.15 ± 1.68**$$## |
| Example 2 | 7 | −1.47 ± 1.28**$$## |
| Example 3 | 8 | −1.36 ± 1.28**## |
| Example 4 | 8 | −2.36 ± 0.98**$$## |
| Example 5 | 8 | −1.92 ± 1.17**$$## |
| Example 6 | 8 | −0.58 ± 1.38** |
| Example 7 | 8 | −0.24 ± 1.66** |
| Comparative example 1 | 8 | −0.22 ± 1.39$$ |
| Comparative example 2 | 7 | −0.92 ± 1.71** |
| Blank control group | 9 | 0.52 ± 1.36 |

Note:
*$P < 0.05$;
**$P < 0.01$; compared with the blank control group
$$P < 0.05$;
$$$P < 0.01$; compared with Comparative example 2
$P < 0.05$;
$P < 0.01$; compared with Example 1

TABLE 4

Changes of the heart rate of the renal hypertensive rats after the application of the patches

| Examples | Number of samples | changes of the heart rate 15 to 28 hours after the application of the patches (BPM) |
|---|---|---|
| Example 1 | 8 | −31.56 ± 17.33##* |
| Example 2 | 7 | −41.62 ± 27.91##**$$ |
| Example 3 | 8 | −31.63 ± 18.37$## |
| Example 4 | 8 | −22.48 ± 13.53##* |
| Example 5 | 8 | −28.62 ± 20.22##* |
| Example 6 | 8 | −17.88 ± 24.02#** |
| Example 7 | 8 | −10.67 ± 17.38**$ |
| Comparative example 1 | 8 | −0.88 ± 24.51$$ |
| Comparative example 2 | 7 | −20.61 ± 5.32** |
| Blank control group | 9 | 4.55 ± 21.28 |

Note:
*$P < 0.05$;
**$P < 0.01$; compared with the blank control group
$$P < 0.05$;
$$$P < 0.01$; compared with Comparative example 2
$P < 0.05$;
$P < 0.01$; compared with Example 1

It can be seen from the above test results that the transdermal patches according to this invention that are formulated from isosorbide dinitrate and Bisoprolol at a certain ratio can significantly enhance the effect of isosorbide dinitrate and Bisoprolol on reducing the pressure respectively and the effect of inhibiting the heart rate.

Test 2. Studies of effects of the acute pressure-reduction on the spontaneous hypertension rats (SHR)

1. Drugs Tested 1.1. A transdermal patch of Example 4, specification: 1.0 mg/cm$^2$, 2.0 mg/cm$^2$ 1.2. A transdermal patch of Comparative example 2, specification: 1.0 mg/cm$^2$ 1.3. Other drugs Bisoprolol Formarate tablets (Bosu): Beijing Four-Ring Pharmaceutical Co., Batch No.: 0501133, specification: 5 mg/tablet Sodium hydroxymethyl cellulose (CMC): Shanghai Chemical Reagent Company of China National Pharmaceutical Group Corp., Batch No.: F20020928, specification: 500 g/package Sodium sulfide: Shanghai Lingfeng Chemical Reagent Ltd., Batch No.: 041115, specification: 500 g/bottle 2. Animals and Groups 2.1. Animals to be Tested Spontaneous hypertensive rats of SPF/VAF grade were provided by Beijing Vitalriver Laboratory Animal Inc. with the certificate Number of SCK (Jing) 2002-0003. The animals' body weight was from 180 to 220 g. All rats were male.

2.2. Grouping of Animals

The SHRs were evenly and randomly divided into 5 groups according to their blood pressure, with each group containing 9 to 10 rats. Said groups were respectively a blank patch control group, high, intermediate and low dosage groups applied with the patch in Example 4, and the positive control group applied with Bosu.

3. Main Experimental Steps 3.1. Experimental Apparatus

The apparatus was BESN-II multiple-channel animal non-invasive manometric system made by Nanjing DeSci Biotech Ltd. Co.

3.2. The Method for Measuring the Blood Pressure of Conscious Rats

A "BESN-II multiple-channel animal non-invasive manometric system" was used in the non-invasive measurement of the blood pressure. After the measurement, data on the systolic arterial pressure (SAP), diastolic pressure (DAP) and heart rate (HR) were collected.

In the acute pressure-reducing tests, the blood pressure was firstly measured for more than 7 days (at least three times), so that the animals would be accustomed to the environment of measuring the blood pressure. After that, tests on the acute pressure-reducing effects were performed. The blood pressure was measured once before the application of the drugs, and the blood pressure and heart rate were recorded. The blood pressure was measured 4 to 6, 9 to 11, 14 to 16, 19 to 21, 27 to 29, 34 to 36, 44 to 46, 50 to 52 and 59 to 61 hours after the application of the drugs. Changes of the blood pressure and heart rate before and after the application of the drugs were recorded.

3.3. Dosages

The transdermal patches of Example 4 were used with the dosages of 20.0 mg of isosorbide dinitrate and Bisoprolol in total/kg body weight (high dosage group), 10.0 mg of isosorbide dinitrate and Bisoprolol in total/kg body weight (intermediate dosage group) and 5.00 mg of isosorbide dinitrate and Bisoprolol in total/kg body weight (low dosage group). Patches with a specification of 2.0 mg/cm$^2$ were used in the high dosage group. The area of said patches used was 10.0 cm$^2$/kg body weight. Patches with a specification of 1.0 mg/cm$^2$ were used in the intermediate and low dosage groups with the areas used 10.0 cm$^2$/kg body weight and 5.0 cm$^2$/kg body weight respectively.

Blank patches with an area of 10.0 cm$^2$/kg body weight were used in the blank control group.

The dosage of the positive drug Bosu applied was 10.0 mg/kg body weight, which is the same as that of the intermediate dosage group of the transdermal patches of Example 4.

A suspension solution was formulated from a Bosu tablet with 0.5% CMC. The concentration of the drug was 1.0 mg/ml.

3.4. The Method of Administration

Drugs to be tested were the patches which were percutaneously and topically applied. Hairs on the back of the rats in an area of 5×5 cm² were removed with 10% sodium sulfide one day prior to the application of the patches. The patches to be tested were topically applied to the naked skin of the rats and then fastened with a medical adhesive tape during the application of the patches.

Bosu was orally applied (p.o.), and the volume of the drug applied was 1.0 ml/100 g body weight.

4. Test results

Effects of the drugs tested on reducing the blood pressure of the spontaneous hypertensive rats were observed. The test results were represented by mean±standard deviation ($\overline{X}\pm SD$). With regard to the statistical treatment, student-T tests among groups were used. The results are shown in table 5.

TABLE 5

Changes of the blood pressure and heart rate of SHR at different times after the application of the patches ($\overline{X} \pm SD$)

| | Hours after the application of the drugs | Control group | Bosu group | Transdermal patch of Example 4 | | |
|---|---|---|---|---|---|---|
| Indexes | | | | High dosage group | Intermediate dosage | Low dosage group |
| SAP (kPa) | 4~6 | 0.23 ± 0.95 | −2.05 ± 1.16** | −3.13 ± 1.47** | −2.69 ± 1.12** | −2.03 ± 0.61** |
| | 27~29 | −0.08 ± 0.73 | −1.03 ± 0.99* | −3.60 ± 0.72** | −2.14 ± 0.71** | −0.92 ± 1.13 |
| | 59~61 | 0.01 ± 1.53 | −0.07 ± 0.93 | −2.23 ± 1.60** | −1.68 ± 1.38* | −1.12 ± 0.65 |
| DAP (kPa) | 4~6 | 0.27 ± 0.54 | −1.30 ± 0.71** | −2.71 ± 1.30** | −2.06 ± 0.52** | −1.48 ± 0.64** |
| | 27~29 | 0.40 ± 0.56 | −0.10 ± 0.64** | −2.33 ± 0.74** | −1.67 ± 0.31** | −0.84 ± 0.79** |
| | 59~61 | −0.52 ± 1.18 | −0.24 ± 0.52** | −1.49 ± 1.29 | −1.75 ± 1.04* | −0.46 ± 0.89 |
| HR (BPM) | 4~6 | −11.5 ± 16.3 | −47.4 ± 12.6** | −47.6 ± 21.9** | −23.1 ± 13.9 | −20.6 ± 20.3 |
| | 27~29 | 2.7 ± 14.2 | −12.2 ± 11.3* | −44.6 ± 14.6** | −17.2 ± 11.1** | −9.9 ± 11.7 |
| | 59~61 | −3.1 ± 21.7 | 2.5 ± 14.7 | −28.9 ± 13.3** | −18.9 ± 22.3 | −12.6 ± 14.3 |

Note:
*$P < 0.05$,
**$P < 0.01$, compared with the control group

Results show that the transdermal patches of Example 4 in the high, intermediate and low dosage groups exhibit significant effect of acutely reducing the blood pressure on the spontaneous hypertensive rats. A significant effect on reducing the blood pressure was exhibited in the high and intermediate dosage groups within 4 to 6 hours after the application of the patches, and a relatively significant effect on reducing the blood pressure was still exhibited within 59 to 61 hours after the application of the patches. In the low dosage group, the effect of reducing the blood pressure could last 27 to 29 hours. The effect in Bosu group could last for 27 to 29 hours.

The transdermal patches of Example 4 in the high, intermediate and low dosage groups exhibited an apparent effect on inhibiting HR. Bosu group also exhibited an apparent effect on inhibiting HR. At the same dosage, the transdermal patch of Example 4 and Bosu had similar effects on inhibiting the heart rate of spontaneous hypertensive rats. However, the pressure-reducing effect of the transdermal patches of Example 4 was apparently potent than that of Bosu.

5. Conclusions

The transdermal patches according to this invention have good pressure-reducing effect on the spontaneous hypertensive rats. The acute pressure-reducing effect is quite potent and can last a long period of time. At the same dosage, the pressure-reducing effect of the transdermal patches according to this invention is obviously potent than that of Bosu, and the duration of the pressure-reducing effect of the transdermal patches according to this invention is longer than that of Bosu. However, the effect of the transdermal patches according to this invention on inhibiting the heart rate is similar to that of Bosu.

Test 3: Studies of therapeutic effects of the pressure-reduction on the spontaneous hypertensive rats (SHRs)

1. Object of the Test

The object of this test is to observe the therapeutic effect of the patches according to this invention on reducing the blood pressure of the spontaneous hypertensive rats.

2. Animals and Groups 2.1. Animals to be Tested

SHRs: the same as described in test 1.

2.2. Grouping of Animals

The SHRs were evenly and randomly divided into 6 groups according to their blood pressure, with each group containing 9 to 10 rats. Said groups were respectively a blank patch control group, high, intermediate and low dosage groups applied with the transdermal patches of Example 4, the group applied with the transdermal patch in Comparative example 2, and the positive control group to which Bosu was administrated orally.

3. Main Experimental Steps 3.1. Experimental Apparatus: the Same as Described in Test 1.

3.2. The Method for Measuring the Blood Pressure of Conscious Rats

In the chronic therapeutically pressure-reducing test, the blood pressure was measured no less than 3 times for at least 10 days before the application of the drugs, so that the animals would be accustomed to the environment for measuring the blood pressure and reliable blood pressure and heart rate data could be obtained. The average values of SAP, DAP and HR measured before the application of the drugs were used as the blood pressure and heart rate data prior to the application of the drugs. And then, the blood pressure was recorded on the $2^{nd}$, $4^{th}$, $6^{th}$ and $8^{th}$ day during the application of the drugs, during which period of time, the blood pressure was recorded about 48 hours after the application of the drugs, i.e. prior to the next application of the drugs. The blood pressure of each group of rats should better be recorded at the same time, and the time difference should not exceed 2 hours.

3.3. Drugs and Dosages

By making a reference to the dosages used in the acute pressure-reducing tests on SHRs, the dosages in the therapeutically pressure-reducing tests on SHRs were 20.0 mg of isosorbide dinitrate and Bisoprolol in total/kg body weight (high dosage group), 10.0 mg of isosorbide dinitrate and Bisoprolol in total/kg body weight (intermediate dosage group) and 5.00 mg of isosorbide dinitrate and Bisoprolol in total/kg body weight (low dosage group) of the transdermal patches of Example 4. Patches with a specification of 2.0 mg/cm² were used in the high dosage group. The area of said patches used was 10.0 cm²/kg body weight. Patches with a specification of 1.0 mg/cm² were used in the intermediate and low dosage groups with the areas used 10.0 cm²/kg body weight and 5.0 cm²/kg body weight respectively.

The patch of Comparative example 2 was used with an area of 10.0 cm²/kg body weight. The dosage was 10.0 mg of Bisoprolol/kg body weight.

Blank patches with an area of 10.0 cm²/kg body weight were used in the blank control group.

Bosu was orally applied (p.o.) in a dosage of 10.0 mg/kg body weight once every two days. A suspension solution was formulated from a Bosu tablet with 0.5% CMC. The concentration of the drug was 1.0 mg/ml.

4. The Method for the Application of the Drugs

The patches in Example 4 and Comparative example 2 were percutaneously and topically applied, and Bosu was orally applied. According to the results of the acute pressure-reducing tests, the duration of the pressure-reducing effect in the high and intermediate dosage groups with regard to the patches of Example 4 could last more than 44 hours after the application of the patches, so that the drugs were applied once every two days in the therapeutically pressure-reducing test. For the patch of Comparative example 2, the drug was also applied once every two days. Bosu was orally applied once every two days.

5. Test Results

The test results were represented by mean±standard deviation ($\bar{X}$±SD). With regard to the statistical treatment, student-T tests among groups were used. The results are shown in tables 6 to 8.

TABLE 6

Influences of the continuous application of the drugs on SAP of SHR

| groups | Dosage mg/kg body weight | Number of animals | Prior to the application of the drugs | SAP and variation after the application of the drugs ($\Delta$) ($\bar{X}$ ± SD, kPa) Days after the application of the drugs | | | |
|---|---|---|---|---|---|---|---|
| | | | | 2 | 4 | 6 | 8 |
| control | | 9 | 27.02 ± 0.54 $\Delta$ | 26.59 ± 0.65# <br> −0.43 ± 0.45 | 26.81 ± 0.43 <br> −0.21 ± 0.66 | 26.65 ± 0.49 <br> −0.36 ± 0.66 | 27.07 ± 0.49 <br> 0.05 ± 0.76 |
| Bosu | 10.0 | 9 | 26.48 ± 0.52 $\Delta$ | 25.72 ± 0.54**## <br> −0.76 ± 0.40 | 25.39 ± 0.67**## <br> −1.09 ± 0.90* | 25.25 ± 0.74**## <br> −1.22 ± 0.83* | 25.24 ± 0.72**## <br> −1.23 ± 0.86** |
| Comparative Example 2 | 10.0 | 8 | 26.57 ± 0.88 $\Delta$ | 25.53 ± 0.62**## <br> −1.04 ± 0.81 | 25.23 ± 0.46**## <br> −1.34 ± 0.59** | 25.15 ± 0.60**## <br> −1.42 ± 0.72** | 24.90 ± 0.62**## <br> −1.67 ± 0.91** |
| Example 4 | 5.0 | 9 | 26.30 ± 0.89 $\Delta$ | 25.94 ± 1.02 <br> −0.36 ± 1.01 | 25.24 ± 0.80**## <br> −1.06 ± 0.86* | 25.20 ± 0.91**# <br> −1.10 ± 1.09 | 24.71 ± 0.57**## <br> −1.59 ± 0.47** |
| | 10.0 | 9 | 26.55 ± 0.63 $\Delta$ | 25.84 ± 0.55*## <br> −0.71 ± 0.25 | 24.65 ± 0.90**## <br> −1.90 ± 0.87** | 24.20 ± 0.68**## <br> −2.35 ± 1.07** | 24.09 ± 0.56**## <br> −2.46 ± 0.79** |
| | 20.0 | 9 | 26.62 ± 0.71 $\Delta$ | 24.43 ± 0.74**## <br> −2.19 ± 0.66** | 24.18 ± 0.86**## <br> −2.44 ± 0.81** | 24.17 ± 0.67**## <br> −2.45 ± 0.66** | 23.44 ± 0.53**## <br> −3.18 ± 0.86** |

Note:
1. *P < 0.05; **P < 0.01; compared with the blank control group
2. #P < 0.05; ##P < 0.01; compared with data prior to the application of the drugs
3. Variation of the blood pressure after the application of the drugs ($\Delta$) = the blood pressure after the application of the drugs − the blood pressure before the application of the drugs

TABLE 7

Influences of the continuous application of the drugs on DAP of SHRs

| groups | Dosage mg/kg body weight | Number of animals | Prior to the application of the drugs | DAP and variation after the application of the drugs ($\Delta$) ($\bar{X}$ ± SD, kPa) Days after the application of the drugs | | | |
|---|---|---|---|---|---|---|---|
| | | | | 2 | 4 | 6 | 8 |
| control | | 9 | 19.98 ± 0.43 $\Delta$ | 20.50 ± 0.92 <br> 0.52 ± 0.74 | 20.27 ± 0.49 <br> 0.29 ± 0.47 | 20.77 ± 0.42## <br> 0.79 ± 0.64 | 20.43 ± 0.73 <br> 0.45 ± 0.98 |
| Bosu | 10.0 | 9 | 19.53 ± 0.49 $\Delta$ | 19.00 ± 0.77*# <br> −0.52 ± 0.63** | 18.71 ± 0.49**## <br> −0.82 ± 0.67** | 18.92 ± 0.47**## <br> −0.61 ± 0.47** | 18.74 ± 0.39**## <br> −0.78 ± 0.48** |
| Comparative Example 2 | 10.0 | 8 | 20.07 ± 0.93 $\Delta$ | 19.20 ± 0.68**## <br> −0.88 ± 0.37** | 18.96 ± 0.95**## <br> −1.11 ± 0.82** | 18.88 ± 0.77**## <br> −1.19 ± 0.75** | 18.82 ± 0.65**## <br> −1.25 ± 0.42** |
| Example 4 | 5.0 | 9 | 19.68 ± 0.59 $\Delta$ | 19.68 ± 1.22 <br> 0.01 ± 1.19 | 19.04 ± 0.77**## <br> −0.63 ± 0.54** | 18.52 ± 0.80**## <br> −1.16 ± 0.81** | 18.65 ± 0.63**## <br> −1.03 ± 0.62** |

TABLE 7-continued

Influences of the continuous application of the drugs on DAP of SHRs

| groups | Dosage mg/kg body weight | Number of animals | Prior to the application of the drugs | DAP and variation after the application of the drugs ($^\Delta$) ($\overline{X} \pm SD$, kPa) | | | |
|---|---|---|---|---|---|---|---|
| | | | | Days after the application of the drugs | | | |
| | | | | 2 | 4 | 6 | 8 |
| | 10.0 | 9 | 19.86 ± 0.68 $^\Delta$ | 19.06 ± 1.17* −0.80 ± 1.41* | 18.38 ± 1.50**# −1.48 ± 1.74** | 18.18 ± 0.73**## −1.68 ± 0.83** | 17.94 ± 0.62**## −1.92 ± 0.44** |
| | 20.0 | 9 | 19.88 ± 0.54 $^\Delta$ | 18.96 ± 0.78**## −0.93 ± 0.61** | 18.06 ± 0.70**## −1.82 ± 0.59** | 17.68 ± 0.73**## −2.21 ± 0.61** | 17.43 ± 0.53**## −2.45 ± 0.58** |

Note:
1. *P < 0.05; **P < 0.01; compared with the blank control group
2. #P < 0.05; ##P < 0.01; compared with data prior to the application of the drugs
3. Variation of the blood pressure after the application of the drugs ($^\Delta$) = the blood pressure after the application of the drugs − the blood pressure before the application of the drugs

TABLE 8

Influences of the continuous application of the drugs on HR of SHR

| groups | Dosage mg/kg body weight | Number of animals | Prior to the application of the drugs | HR and variation after the application of the drugs ($^\Delta$)(BPM) | | | |
|---|---|---|---|---|---|---|---|
| | | | | Days after the application of the drugs | | | |
| | | | | 2 | 4 | 6 | 8 |
| control | | 9 | 402.2 ± 11.3 $^\Delta$ | 401.2 ± 14.8 −0.9 ± 4.8 | 398.4 ± 10.4 −3.7 ± 11.4 | 398.1 ± 21.3 −4.1 ± 14.0 | 401.7 ± 11.4 −0.5 ± 11.3 |
| Bosu | 10.0 | 9 | 401.6 ± 10.5 $^\Delta$ | 393.2 ± 13.4 −8.3 ± 12.2 | 384.1 ± 11.5*## −17.5 ± 12.0* | 383.7 ± 15.5## −17.9 ± 11.8* | 380.4 ± 9.5**## −21.1 ± 9.2** |
| Comparative Example 2 | 10.0 | 8 | 402.7 ± 10.6 $^\Delta$ | 389.4 ± 13.6## −13.4 ± 6.1** | 382.3 ± 11.2**## −20.5 ± 7.6** | 373.1 ± 11.0**## −29.6 ± 12.5** | 376.9 ± 8.7**## −25.9 ± 9.** |
| Example 4 | 5.0 | 9 | 396.3 ± 13.8 $^\Delta$ | 389.7 ± 23.6 −6.7 ± 18.1 | 385.0 ± 13.7# −11.3 ± 10.9 | 380.4 ± 14.6## −15.9 ± 9.2* | 377.3 ± 12.3**## −19.0 ± 11.7** |
| | 10.0 | 9 | 408.6 ± 8.0 $^\Delta$ | 397.9 ± 15.4# −10.8 ± 13.7 | 382.3 ± 11.6**# −26.3 ± 8.1** | 384.6 ± 11.9## −24.1 ± 10.4** | 382.1 ± 12.1**## −26.5 ± 12.5** |
| | 20.0 | 9 | 411.6 ± 9.1 $^\Delta$ | 393.1 ± 16.8## −18.5 ± 9.7** | 380.0 ± 14.9**## −31.6 ± 12.1** | 372.6 ± 14.4**## −39.1 ± 10.5** | 376.8 ± 14.2**## −34.9 ± 13.6** |

Note:
1. *P < 0.05; **P < 0.01; compared with the blank control group
2. #P < 0.05; ##P < 0.01; compared with data prior to the application of the drugs
3. Variation of the heart rate after the application of the drugs ($^\Delta$) = the heart rate after the application of the drugs − the heart rate before the application of the drugs It can be seen from the results in tables 6 to 8 that the extent of the reduction of the blood pressure was stable after the drugs were applied for 4 consecutive days. The transdermal patches according to this invention exhibited a significant effect on inhibiting HR, namely that the HR in the intermediate and high dosage groups could be apparently lowered during the application of the patches.

Bosu could also exhibit certain effects on reducing the blood pressure and inhibiting the heart rate, which were less potent. The transdermal patch of Comparative example 2 also exhibited significant effects on reducing the blood pressure and inhibiting the heart rate.

At the same dosage, the pressure-reducing effect of the transdermal patches according to this invention was apparently potent than that of the transdermal patch of Comparative example 2 and Bosu, but the effects on inhibiting the heart rate of said three formulations were similar.

During the tests, the blood pressure and heart rate in the control group were not significantly changed.

Test 4: Studies on the pharmacodynamic action of the drugs for anti-myocardial ischemia 1. Object of the Test The object of this test is to observe the effect of transdermal patches of this invention on myocardial ischemia and compare it with that of oral isosorbide dinitrate tablets.

2. Experimental Materials

Animals: SD rats (second class), male, weighing 180-200 g, bought from Institute of Laboratory Animal Science, Chinese Academy of Medical Science, certificate number: SCXK11-00-0006

Instrument: Eelectrocardiograph (ECG-6511, Shanghai Kohden (?)Medical Electronic Instrument Corporation)

Reagent: isosorbide dinitrate tablets (Shandong Boshan Pharmaceutic Coporation LTD., formulated to be a suspension at a concentration of 0.1042 mg/mL by adding water immediately before it was used)

3. Experimental Method

The rats were divided into 5 groups according to their weight, namely normal group, model group, isosorbide dinitrate tablets control group, and high (3.8 mg/kg body weight) and low (1.9 mg/kg body weight) dosage groups of the transdermal patches of Example 4. Before the experiment started, hairs were removed from the back of the rats except those of isosorbide dinitrate tablets control group. The patches to be tested were topically applied to the back skin of the rats and then fixed with a medical adhesive tape. Timing was started. The blank patches were applied on the animals of the model group. The suspension of isosorbide dinitrate tablets (0.1042 mg/mL) was administered by means of a gavage to the animals in the isosorbide dinitrate tablets control group one hour before the experiment started. The animals in the patches groups were weighed 15 hours after the application of patches, and were anesthetized abdominally with 15% urethane (commercially available from Chongqing Chemical Reagent Factory, Batch Number: 030706, which was formulated to be a 15% solution by being dissolved into water under heating) solution. The electrocardiogram of the animals was measured before the operation. The thoracic cavity of the animals was then opened, and the coronary arteries were ligated. The same was done to the animals in the normal group, but their coronary arteries were not ligated. The electroncardiogram of the animals was measured right after the operation or 2, 4 and 6 hours after the operation. Then, the abdominal cavity of the animals was opened, and 2 ml blood sample was taken from the abdominal aorta of each the animals and was centrifugalized. The supernate obtained therefrom was assayed to measure serum lactate dehydrogenase (LDH), aspartyltransferase (AST) and creatine kinase (CK). The heart of the animals was then taken out and frozen until being hardened. The heart was cut from cardiac apex to the site of deligation, and was sliced to 3-4 pieces, which were stained using NBT, then dried out by means of filter papers. The stained part was cut off, which part was an ischemic region, the remainder was a non-ischemic region. The ischemic region and the non-ischemic region were weighed respectively and the percentage of myocardial infarct can be calculated based on the ratio:

the ischemic region/(the ischemic region+the non-ischemic region).

The effects of the drugs on anti-myocardial ischemia were evaluated by analyzing the increment of T wave at different times before and after the application of drugs, calculating the cardiac muscle enzyme of each group, and statistically analyzing the data obtained.

4. The Outcome of the Pharmacodynamic Study

The following effects of the transdermal patches of this invention on the rats whose coronary artery were deligated were observed: the rise of the electrocardiogram T wave (mV), the resistance to the increasing of cardiac muscle enzyme and the degree of myocardial infarct. Compared with the rats administered with isosorbide dinitrate tablets, the data obtained are indicated in Table 9-11.

TABLE 9

The effect on the rise of T wave (mV) of electrocardiogram

| Group | non-deligation | Instantly after deligation | after the deligation | | |
|---|---|---|---|---|---|
| | | | 2 hous | 4 hours | 6 hours |
| normal group | 0 | 0.03 ± 0.11 | 0.01 ± 0.083 | 0.06 ± 0.069 | 0.04 ± 0.092 |
| model group | 0 | 2.45 ± 2.07## | 1.68 ± 1.84## | 1.50 ± 1.33## | 1.67 ± 1.6## |
| isosorbide dinitrate tablets control group (1.9 mg/kg body weight) | 0 | 1.39 ± 0.72 | 0.53 ± 0.49 | 0.45 ± 0.70* | 0.23 ± 0.5** |
| low dosage group of the patch in Example 4 (1.9 mg/kg body weight) | 0 | 0.46 ± 0.047 | 0.20 ± 0.096 | 0.10 ± 0.067** | 0.04 ± 0.094** |
| high dosage group of the patch in Example 4 (3.8 mg/kg body weight) | 0 | 0.35 ± 1.08 | 0.00 ± 0.105* | 0.00 ± 0.075** | −0.10 ± 0.025** |

Note:
$P < 0.01$, compared with the normal group;
*$P < 0.05$,
**$P < 0.01$, compared with the model group

TABLE 10

The effect on the resistance to the increase of cardiac muscle enzyme in serum

| groups | Lactate dehydrogenase (LDH) | Aspartyltransferase (AST) | Creatine kinase (CK) |
|---|---|---|---|
| normal group | 502.7 ± 183.6 | 170.3 ± 28.4 | 1155.1 ± 385.6 |
| model group | 891.1 ± 108.8# | 339.3 ± 40.84## | 1982.2 ± 730.6# |
| isosorbide dinitrate tablets control group (1.9 mg/kg body weight) | 682 ± 132.1* | 256 ± 29.9** | 1348.7 ± 555.1 |
| low dosage group of the patch in Example 4 (1.9 mg/kg body weight) | 819.1 ± 131.9 | 268.6 ± 59.4* | 1344.1 ± 438.9 |
| high dosage group of the patch in Example 4 (3.8 mg/kg body weight) | 796.9 ± 178.4 | 281.3 ± 74.4* | 1324.6 ± 557.3* |

Note:
$P < 0.05$,
$P < 0.01$, compared with the normal group;
*$P < 0.05$,
**$P < 0.01$, compared with the model group

TABLE 11

The effect on the degree of myocardial infarct (%)

| groups | dosage | degree of infarct (%) |
|---|---|---|
| model group | — | 10.9 ± 2.2 |
| isosorbide dinitrate tablets control group | 1.9 mg/kg body weight | 7.2 ± 1.7** |
| low dosage group of the patch in Example 4 (1.9 mg/kg body weight) | 1.9 mg/kg body weight | 6.0 ± 1.88** |
| high dosage group of the patch in Example 4 | 3.8 mg/kg body weight | 6.2 ± 1.49** |

Note:
*P < 0.05,
**P < 0.01, compared with the model group

It can be seen from Tables 9 to 11 that the percentage of myocardial infarct in the model group was approximately 11% 21 hours after the application of the drugs (i.e., 6 hours after the deligation). There is an evidently lower percentage of myocardial infarct in the two groups at different dosages of transdermal patches, which is the same as or lower than the isosorbide dinitrate tablets group. The cardiac muscle enzyme increased significantly for the model group, which indicated that cardiac muscle cells were injured after deligation, and cardiac muscle enzyme leakage was caused. Aspartyltransferase and creatine kinase decreased dramatically after the application of the drugs, and the cardiac muscle injury was apparently alleviated. The T wave for the model group rised dramatically 2 hours after the coronary artery was deligated, and didn't fall until the end of the experiment. The T wave for the patch groups and the tablets group fell dramatically 2 hours after the coronary artery was deligated (17 hours after application of the patches), and the effect lasted until the end of the experiment (6 hours after the deligation).

The results indicated that the transdermal patches of this invention had equivalent or better effect on the myocardial ischemia model induced by deligation of coronary artery in comparison with the isosorbide dinitrate tablets.

The above outcome suggested that transdermal patches of this invention had better preventive and therapeutic effects on various heart diseases.

What is claimed:

1. A transdermal drug delivery patch in the form of a layer complex, comprising a backing layer, a drug-reservoir layer comprising pharmacologically active ingredients and pharmaceutically acceptable adjuvants, and a release liner covering the drug-reservoir layer, characterized in that the drug-reservoir layer comprises, as pharmacologically active ingredients, isosorbide dinitrate and Bisoprolol at a ratio of 1:3 to 3:1 by weight.

2. The transdermal patch according to claim 1, wherein the pharmaceutically acceptable adjuvants include a permeation enhancer and a polymeric matrix.

3. The transdermal patch according to claim 2, wherein the permeation enhancer is selected from the group consisting of surfactants, organic solvents, dimethyl sulfoxide and analogs thereof, 1 dodecylazecycloheptan-2-one, organic acids and esters or amides thereof, and a mixture thereof.

4. The transdermal patch according to claim 3, wherein the permeation enhancer is selected from the group consisting of isopropyl myristate, 1-dodecylazecycloheptan-2-one, propylene glycol and a mixture thereof.

5. The transdermal patch according to claim 2, wherein the polymeric matrix is selected from the group consisting of an acrylic pressure-sensitive adhesive or a combination of an acrylic pressure-sensitive adhesive with an acrylic resin selected from the group consisting of Poly(methacylic acid-co-methyl methacrylate 1:1 Poly(methacylic acid-co-methyl methacrylate 1:2, Poly(ethyl acrylate-co-methyl methacrylate-co-trimethylammonioethyl methacrylate chloride) 1:2:0.2 in a form of granules or fine powders Poly(ethyl acrylate-co-methyl methacrylate-co-trimethylammonioethyl methacrylate chloride) 1:2:0.1 in a form of granules or fine powders, Poly(butyl methacrylate-co-(2-dimethylaminoethyl)methacrylate-co-methyl methacrylate) 1:2:1 in a form of granules or fine powders, Poly(ethyl acrylate-co-methacrylic acid) 1:1 and a mixture thereof.

6. The transdermal patch according to claim 5, wherein the polymeric matrix is a mixture of on the acrylic pressure-sensitive adhesive with the acrylic resin, and/or the acrylic pressure-sensitive adhesive is prepared by copolymerizing the monomers selected from acrylic acid, butyl acrylate, 2-ethylhexyl acrylate, vinyl acetate, 2-hydroxyethyl acrylic acid or a combination thereof.

7. The transdermal patch according to claim 6, wherein the acrylic pressure-sensitive adhesive is prepared by copolymerizing the monomers of butyl acrylate, 2-ethylhexyl acrylate, and vinyl acetate.

8. A transdermal patch according to claim 1, wherein the backing layer consists of an aluminum foil, polyethylene terephthalate, polyethylene or non-woven fabrics.

9. The transdermal patch according to claim 1, wherein the drug-reservoir layer is consisting of the following components:

| | |
|---|---|
| isosorbide dinitrate | 1-17% |
| Bisoprolol | 1-17% |
| Poly(ethyl acrylate-co-methyl methacrylate-co-trimethylammonioethyl methacrylate chloride) 1:2:0.1 | 0.1-30% |
| acrylic resin pressure-sensitive adhesive (in dry basis) | 30-80% |
| propylene glycol | 0-25% |
| isopropyl myristate | 4.5-22% |
| 1-dodecylazecycloheptan-2-one | 1.5-7% | the contents of the components are based on the total weight of the drug-reservoir layer, and the sum thereof is 100%.

10. The transdermal patch according to claim 9, wherein the drug-reservoir layer is consisting of the following components:

| | |
|---|---|
| isosorbide dinitrate | 2.5-15% |
| Bisoprolol | 2-8% |
| Poly(ethyl acrylate-co-methyl methacrylate-co-trimethylammonioethyl methacrylate chloride) 1:2:0.1 | 0.5-25% |
| acrylic resin pressure-sensitive adhesive (in dry basis) | 45-65% |
| isopropyl myristate | 6-10% |
| 1-dodecylazecycloheptan-2-one | 4-6% | the contents of the components are based on the total weight of the drug-reservoir layer, and the sum thereof is 100%.

11. The transdermal patch according to claim 10, wherein the drug-reservoir layer is consisting of the following components:

| | |
|---|---|
| isosorbide dinitrate | 3.6-10% |
| Bisoprolol | 2.6-6% |
| Poly(ethyl acrylate-co-methyl methacrylate-co-trimethylammonioethyl methacrylate chloride) 1:2:0.1 | 3-25% |
| acrylic resin pressure-sensitive adhesive (in dry basis) | 45-65% |
| isopropyl myristate | 6-10% |
| 1-dodecylazecycloheptan-2-one | 4-6% | the contents of the components are based on the total weight of the drug-reservoir layer, and the sum thereof is 100%.

12. The transdermal patch according to claim 1, wherein the drug-reservoir layer is consisting of the following components:

| | |
|---|---|
| isosorbide dinitrate | 0.5-2 parts by weight |
| Bisoprolol | 0.4-1.1 parts by weight |
| Poly(ethyl acrylate-co-methyl methacrylate-co-trimethylammonioethyl methacrylate chloride) 1:2:0.1 | 0.1-3.5 parts by weight |
| acrylic resin pressure-sensitive adhesive (in dry basis) | 5-10 parts by weight |
| isopropyl myristate | 0.5-2 parts by weight |
| 1-dodecylazecycloheptan-2-one | 0.2-0.6 part by weight. |

13. The transdermal patch according to claim 12, wherein the drug-reservoir layer is consisting of the following components:

| | |
|---|---|
| isosorbide dinitrate | 0.5-1.3 parts by weight |
| Bisoprolol | 0.35-0.8 part by weight |
| Poly(ethyl acrylate-co-methyl methacrylate-co-trimethylammonioethyl methacrylate chloride) 1:2:0.1 | 0.5-3.5 parts by weight |
| acrylic resin pressure-sensitive adhesive (in dry basis) | 6-8 parts by weight |
| isopropyl myristate | 1-1.5 parts by weight |
| 1-dodecylazecycloheptan-2-one | 0.2-0.6 part by weight. |

14. The transdermal patch according to claim 13, wherein the drug-reservoir layer is consisting of the following components:

| | |
|---|---|
| isosorbide dinitrate | 0.5-0.7 part by weight |
| Bisoprolol | 0.4 part by weight |
| Poly(ethyl acrylate-co-methyl methacrylate-co-trimethylammonioethyl methacrylate chloride) 1:2:0.1 | 0.25-3.5 parts by weight |
| acrylic resin pressure-sensitive adhesive (in dry basis) | 6-8 parts by weight |
| isopropyl myristate | 1-1.5 parts by weight |
| 1-dodecylazecycloheptan-2-one | 0.2-0.6 part by weight. |

15. The transdermal patch according to claim 14, wherein the drug-reservoir layer is consisting of the following components:

| | |
|---|---|
| isosorbide dinitrate | 0.6 part by weight |
| Bisoprolol | 0.4 part by weight |
| Poly(ethyl acrylate-co-methyl methacrylate-co-trimethylammonioethyl methacrylate chloride) 1:2:0.1 | 3 parts by weight |
| acrylic resin pressure-sensitive adhesive (in dry basis) | 6-8 parts by weight |
| isopropyl myristate | 1-1.5 parts by weight |
| 1-dodecylazecycloheptan-2-one | 0.4 part by weight. |

16. The transdermal patch according to claim 12, wherein the drug-reservoir layer is consisting of the following components:

| | |
|---|---|
| isosorbide dinitrate | 1.0-1.5 parts by weight |
| Bisoprolol | 0.8 part by weight |
| Poly(ethyl acrylate-co-methyl methacrylate-co-trimethylammonioethyl methacrylate chloride) 1:2:0.1 | 0.25-3.5 parts by weight |
| acrylic resin pressure-sensitive adhesive (in dry basis) | 6-8 parts by weight |
| isopropyl myristate | 1-1.5 parts by weight |
| 1-dodecylazecycloheptan-2-one | 0.2-0.6 part by weight. |

17. The transdermal patch according to claim 16, wherein the drug-reservoir layer is consisting of the following components:

| | |
|---|---|
| isosorbide dinitrate | 1.2 parts by weight |
| Bisoprolol | 0.8 part by weight |
| Poly(ethyl acrylate-co-methyl methacrylate-co-trimethylammonioethyl methacrylate chloride) 1:2:0.1 | 3 parts by weight |
| acrylic resin pressure-sensitive adhesive (in dry basis) | 6-8 parts by weight |
| isopropyl myristate | 1-1.5 parts by weight |
| 1-dodecylazecycloheptan-2-one | 0.4 part by weight. |

18. A transdermal patch according to claim 1 wherein the drug-reservoir layer is in the form of a mono-layer or multi-layered complex.

19. A transdermal patch according to claim 1 for treating or preventing hypertension, coronary heart disease, atherosclerosis, myocardial ischemia or angina pectoris in mammals.

20. A method for treating or preventing hypertension, coronary heart disease, atherosclerosis, myocardial ischemia or angina pectoris in mammals, comprises topically applying transdermal patch according to claim 1 to mammals.

21. A method according to claim 20, in which the patch is topically applied to mammals in a dose of, based on the total weight of the isosorbide dinitrate and Bisoprolol, 0.05-20 mg/kg body weight per day.

22. The transdermal patch according to claim 1, wherein the ratio of isosorbide dinitrate to Bisoprolol is 1.2 to 1.8:1 by weight.

23. The transdermal patch according to claim 1, wherein the ratio of isosorbide dinitrate to Bisoprolol is 1.4 to 1.6:1 by weight.

* * * * *